United States Patent
Mullen

(10) Patent No.: US 8,302,872 B2
(45) Date of Patent: Nov. 6, 2012

(54) ADVANCED DYNAMIC CREDIT CARDS

(75) Inventor: Jeffrey D. Mullen, Pittsburgh, PA (US)

(73) Assignee: Dynamics Inc., Pittsburgh, PA (US)

( * ) Notice: Subject to any disclaimer, the term of this patent is extended or adjusted under 35 U.S.C. 154(b) by 0 days.

(21) Appl. No.: 13/187,454

(22) Filed: Jul. 20, 2011

(65) Prior Publication Data

US 2011/0272479 A1 Nov. 10, 2011

Related U.S. Application Data

(63) Continuation of application No. 12/339,065, filed on Dec. 19, 2008.

(60) Provisional application No. 61/016,491, filed on Dec. 24, 2007, provisional application No. 61/026,846, filed on Feb. 7, 2008, provisional application No. 61/027,807, filed on Feb. 11, 2008, provisional application No. 61/081,003, filed on Jul. 15, 2008, provisional application No. 61/086,239, filed on Aug. 5, 2008, provisional application No. 61/090,423, filed on Aug. 20, 2008, provisional application No. 61/097,401, filed on Sep. 16, 2008, provisional application No. 61/112,766, filed on Nov. 9, 2008, provisional application No. 61/117,186, filed on Nov. 23, 2008, provisional application No. 61/119,366, filed on Dec. 2, 2008, provisional application No. 61/120,813, filed on Dec. 8, 2008.

(51) Int. Cl.
*G06K 19/06* (2006.01)
*G06K 19/00* (2006.01)
*G06K 5/00* (2006.01)
*G06Q 40/00* (2012.01)
*G07D 11/00* (2006.01)
*G07F 19/00* (2006.01)

(52) U.S. Cl. ........ 235/493; 235/379; 235/380; 235/487; 235/492

(58) Field of Classification Search .......... 235/379–381, 235/487, 492–493; 705/41–44
See application file for complete search history.

(56) References Cited

U.S. PATENT DOCUMENTS

| | | | |
|---|---|---|---|
| 4,353,064 A | 10/1982 | Stamm | |
| 4,394,654 A | 7/1983 | Hofmann-Cerfontaine | |
| 4,614,861 A | 9/1986 | Pavlov et al. | |
| 4,667,087 A | 5/1987 | Quintana | |
| 4,701,601 A * | 10/1987 | Francini et al. | 235/449 |
| 4,720,860 A | 1/1988 | Weiss | |

(Continued)

FOREIGN PATENT DOCUMENTS

EP 0203683 12/1986

(Continued)

OTHER PUBLICATIONS

U.S. Appl. No. 60/594,300, Poidomani et al.

(Continued)

*Primary Examiner* — Daniel Walsh

(57) ABSTRACT

A credit card is provided that may include a credit card number, where at least a portion of the credit card number changes periodically. A magnetic emulator and/or magnetic stripe encoder may be provided to communicate at least a portion of the information needed to complete a credit card transaction to a credit card reader. For example, a magnetic emulator may be provided about a magnetic stripe so that the magnetic emulator communicates the information that changes and the magnetic stripe communicates the information that does not change. In doing so, the amount of power used by a credit card may be reduced with respect to a credit card that communicates, for example, all of the information with a magnetic emulator.

18 Claims, 8 Drawing Sheets

U.S. PATENT DOCUMENTS

| | | | |
|---|---|---|---|
| 4,786,791 A * | 11/1988 | Hodama | 235/449 |
| 4,789,776 A | 12/1988 | Inoue | |
| 4,791,283 A * | 12/1988 | Burkhardt | 235/438 |
| 4,797,542 A | 1/1989 | Hara | |
| 4,880,963 A | 11/1989 | Yamashita | |
| 4,902,146 A | 2/1990 | Ishikawa | |
| 5,038,251 A | 8/1991 | Sugiyama et al. | |
| 5,168,520 A | 12/1992 | Weiss | |
| 5,237,614 A | 8/1993 | Weiss | |
| 5,254,843 A | 10/1993 | Hynes et al. | |
| 5,276,311 A | 1/1994 | Hennige | |
| 5,281,799 A | 1/1994 | McIntire et al. | |
| 5,347,580 A | 9/1994 | Molva et al. | |
| 5,359,183 A | 10/1994 | Skodlar | |
| 5,361,062 A | 11/1994 | Weiss et al. | |
| 5,412,199 A | 5/1995 | Finkelstein et al. | |
| 5,434,398 A | 7/1995 | Goldberg | |
| 5,434,405 A | 7/1995 | Finkelstein et al. | |
| 5,477,038 A | 12/1995 | Levine et al. | |
| 5,478,994 A | 12/1995 | Rahman | |
| 5,479,512 A | 12/1995 | Weiss | |
| 5,484,997 A | 1/1996 | Haynes | |
| 5,485,519 A | 1/1996 | Weiss | |
| 5,585,787 A | 12/1996 | Wallerstein | |
| 5,591,949 A | 1/1997 | Bernstein | |
| 5,608,203 A | 3/1997 | Finkelstein et al. | |
| 5,623,552 A | 4/1997 | Lane | |
| 5,657,388 A | 8/1997 | Weiss | |
| 5,748,737 A | 5/1998 | Daggar | |
| 5,763,868 A | 6/1998 | Kubota et al. | |
| 5,834,747 A | 11/1998 | Cooper | |
| 5,834,756 A | 11/1998 | Gutman et al. | |
| 5,844,230 A | 12/1998 | Lalonde | |
| 5,856,661 A | 1/1999 | Finkelstein et al. | |
| 5,864,623 A | 1/1999 | Messina et al. | |
| 5,883,377 A | 3/1999 | Chapin, Jr. | |
| 5,886,874 A | 3/1999 | Onoda et al. | |
| 5,907,142 A | 5/1999 | Kelsey | |
| 5,913,203 A | 6/1999 | Wong et al. | |
| 5,937,394 A | 8/1999 | Wong et al. | |
| 5,955,021 A | 9/1999 | Tiffany, III | |
| 5,955,961 A * | 9/1999 | Wallerstein | 340/5.4 |
| 5,956,699 A | 9/1999 | Wong et al. | |
| 5,999,624 A | 12/1999 | Hopkins | |
| 6,012,636 A | 1/2000 | Smith | |
| 6,025,054 A | 2/2000 | Tiffany, III | |
| 6,045,043 A | 4/2000 | Bashan et al. | |
| 6,076,163 A | 6/2000 | Hoffstein et al. | |
| 6,085,320 A | 7/2000 | Kaliski | |
| 6,095,416 A | 8/2000 | Grant et al. | |
| 6,129,277 A | 10/2000 | Grant et al. | |
| 6,130,621 A | 10/2000 | Weiss | |
| 6,145,079 A | 11/2000 | Mitty et al. | |
| 6,157,920 A | 12/2000 | Jakobsson et al. | |
| 6,161,181 A | 12/2000 | Haynes, III et al. | |
| 6,176,430 B1 | 1/2001 | Finkelstein et al. | |
| 6,182,894 B1 | 2/2001 | Hackett et al. | |
| 6,189,098 B1 | 2/2001 | Kaliski | |
| 6,199,052 B1 | 3/2001 | Mitty et al. | |
| 6,206,293 B1 | 3/2001 | Gutman et al. | |
| 6,240,184 B1 | 5/2001 | Huynh et al. | |
| 6,241,153 B1 | 6/2001 | Tiffany, III | |
| 6,256,873 B1 | 7/2001 | Tiffany, III | |
| 6,269,163 B1 | 7/2001 | Rivest et al. | |
| 6,286,022 B1 | 9/2001 | Kaliski et al. | |
| 6,308,890 B1 | 10/2001 | Cooper | |
| 6,313,724 B1 | 11/2001 | Osterweil | |
| 6,389,442 B1 | 5/2002 | Yin et al. | |
| 6,393,447 B1 | 5/2002 | Jakobsson et al. | |
| 6,398,115 B2 | 6/2002 | Krause | |
| 6,402,029 B1 | 6/2002 | Gangi | |
| 6,411,715 B1 | 6/2002 | Liskov et al. | |
| 6,446,052 B1 | 9/2002 | Juels | |
| 6,460,141 B1 | 10/2002 | Olden | |
| 6,592,044 B1 | 7/2003 | Wong et al. | |
| 6,607,127 B2 | 8/2003 | Wong | |
| 6,609,654 B1 | 8/2003 | Anderson et al. | |
| 6,631,849 B2 | 10/2003 | Blossom | |
| 6,655,585 B2 | 12/2003 | Shinn | |
| 6,681,988 B2 | 1/2004 | Stack et al. | |
| 6,705,520 B1 | 3/2004 | Pitroda et al. | |
| 6,755,341 B1 | 6/2004 | Wong et al. | |
| 6,764,005 B2 | 7/2004 | Cooper | |
| 6,769,618 B1 | 8/2004 | Finkelstein | |
| 6,805,288 B2 | 10/2004 | Routhenstein et al. | |
| 6,811,082 B2 | 11/2004 | Wong | |
| 6,813,354 B1 | 11/2004 | Jakobsson et al. | |
| 6,817,532 B2 | 11/2004 | Finkelstein | |
| 6,873,974 B1 | 3/2005 | Schutzer | |
| 6,902,116 B2 | 6/2005 | Finkelstein | |
| 6,970,070 B2 | 11/2005 | Juels et al. | |
| 6,975,205 B1 | 12/2005 | French et al. | |
| 6,980,969 B1 | 12/2005 | Tuchler et al. | |
| 6,985,583 B1 | 1/2006 | Brainard et al. | |
| 6,991,155 B2 | 1/2006 | Burchette, Jr. | |
| 7,013,030 B2 | 3/2006 | Wong et al. | |
| 7,035,443 B2 | 4/2006 | Wong | |
| 7,039,223 B2 | 5/2006 | Wong | |
| 7,044,394 B2 | 5/2006 | Brown | |
| 7,051,929 B2 | 5/2006 | Li | |
| 7,083,094 B2 | 8/2006 | Cooper | |
| 7,097,108 B2 | 8/2006 | Zellner et al. | |
| 7,100,049 B2 | 8/2006 | Gasparini et al. | |
| 7,100,821 B2 | 9/2006 | Rasti | |
| 7,111,172 B1 | 9/2006 | Duane et al. | |
| 7,114,652 B2 | 10/2006 | Moullette et al. | |
| 7,136,514 B1 | 11/2006 | Wong | |
| 7,140,550 B2 | 11/2006 | Ramachandran | |
| 7,163,153 B2 | 1/2007 | Blossom | |
| 7,195,154 B2 | 3/2007 | Routhenstein | |
| 7,197,639 B1 | 3/2007 | Juels et al. | |
| 7,219,368 B2 | 5/2007 | Juels et al. | |
| 7,225,537 B2 | 6/2007 | Reed | |
| 7,225,994 B2 | 6/2007 | Finkelstein | |
| 7,246,752 B2 | 7/2007 | Brown | |
| 7,298,243 B2 | 11/2007 | Juels et al. | |
| 7,334,732 B2 | 2/2008 | Cooper | |
| 7,337,326 B2 | 2/2008 | Palmer et al. | |
| 7,346,775 B2 | 3/2008 | Gasparini et al. | |
| 7,356,696 B1 | 4/2008 | Jakobsson et al. | |
| 7,357,319 B1 | 4/2008 | Lin et al. | |
| 7,359,507 B2 | 4/2008 | Kaliski | |
| 7,360,688 B1 | 4/2008 | Harris | |
| 7,363,494 B2 | 4/2008 | Brainard et al. | |
| 7,380,710 B2 | 6/2008 | Brown | |
| 7,398,253 B1 | 7/2008 | Pinnell | |
| 7,404,087 B2 | 7/2008 | Teunen | |
| 7,424,570 B2 | 9/2008 | D'Albore et al. | |
| 7,427,033 B1 | 9/2008 | Roskind | |
| 7,454,349 B2 | 11/2008 | Teunen et al. | |
| 7,461,250 B1 | 12/2008 | Duane et al. | |
| 7,461,399 B2 | 12/2008 | Juels et al. | |
| 7,472,093 B2 | 12/2008 | Juels | |
| 7,472,829 B2 * | 1/2009 | Brown | 235/382.5 |
| 7,494,055 B2 | 2/2009 | Fernandes et al. | |
| 7,500,603 B2 | 3/2009 | McCaskey et al. | |
| 7,502,467 B2 | 3/2009 | Brainard et al. | |
| 7,502,933 B2 | 3/2009 | Jakobsson et al. | |
| 7,503,485 B1 | 3/2009 | Routhenstein | |
| 7,516,492 B1 | 4/2009 | Nisbet et al. | |
| 7,523,301 B2 | 4/2009 | Nisbet et al. | |
| 7,530,495 B2 | 5/2009 | Cooper | |
| 7,532,104 B2 | 5/2009 | Juels | |
| 7,543,739 B2 | 6/2009 | Brown et al. | |
| 7,559,464 B2 | 7/2009 | Routhenstein | |
| 7,562,221 B2 | 7/2009 | Nystrom et al. | |
| 7,562,222 B2 | 7/2009 | Gasparini et al. | |
| 7,580,898 B2 | 8/2009 | Brown et al. | |
| 7,581,678 B2 * | 9/2009 | Narendra et al. | 235/451 |
| 7,584,153 B2 | 9/2009 | Brown et al. | |
| 7,591,416 B2 * | 9/2009 | Blossom | 235/380 |
| 7,591,426 B2 | 9/2009 | Osterweil et al. | |
| 7,591,427 B2 | 9/2009 | Osterweil | |
| 7,602,904 B2 | 10/2009 | Juels et al. | |
| 7,621,458 B2 | 11/2009 | Zellner et al. | |
| 7,631,804 B2 | 12/2009 | Brown | |
| 7,639,537 B2 | 12/2009 | Sepe et al. | |

| Patent/Publication | Date | Inventor(s) | Class |
|---|---|---|---|
| 7,641,124 B2 | 1/2010 | Brown et al. | |
| 7,660,902 B2 | 2/2010 | Graham et al. | |
| 7,681,232 B2 | 3/2010 | Nordentoft et al. | |
| 7,784,687 B2 | 8/2010 | Mullen et al. | |
| 7,828,207 B2 | 11/2010 | Cooper | |
| 7,954,724 B2* | 6/2011 | Poidomani et al. | 235/492 |
| 8,011,577 B2 | 9/2011 | Mullen et al. | |
| 8,020,775 B2* | 9/2011 | Mullen et al. | 235/493 |
| 8,074,877 B2 | 12/2011 | Mullen et al. | |
| 8,103,881 B2* | 1/2012 | Doughty et al. | 713/186 |
| 2001/0034702 A1 | 10/2001 | Mockett et al. | |
| 2001/0047335 A1 | 11/2001 | Arndt et al. | |
| 2002/0003169 A1 | 1/2002 | Cooper | |
| 2002/0043566 A1* | 4/2002 | Goodman et al. | 235/492 |
| 2002/0059114 A1 | 5/2002 | Cockrill et al. | |
| 2002/0070976 A1 | 6/2002 | Tanner et al. | |
| 2002/0082989 A1 | 6/2002 | Fife et al. | |
| 2002/0092914 A1 | 7/2002 | Pentz et al. | |
| 2002/0096570 A1 | 7/2002 | Wong et al. | |
| 2002/0120583 A1 | 8/2002 | Keresman, III et al. | |
| 2002/0123967 A1* | 9/2002 | Wang | 705/51 |
| 2002/0153424 A1* | 10/2002 | Li | 235/492 |
| 2002/0185543 A1 | 12/2002 | Pentz et al. | |
| 2003/0034388 A1 | 2/2003 | Routhenstein et al. | |
| 2003/0052168 A1 | 3/2003 | Wong | |
| 2003/0057278 A1 | 3/2003 | Wong | |
| 2003/0116635 A1 | 6/2003 | Taban | |
| 2003/0145205 A1 | 7/2003 | Sarcanin | |
| 2003/0152253 A1 | 8/2003 | Wong | |
| 2003/0163287 A1 | 8/2003 | Vock et al. | |
| 2003/0173409 A1 | 9/2003 | Vogt et al. | |
| 2003/0179909 A1 | 9/2003 | Wong et al. | |
| 2003/0179910 A1 | 9/2003 | Wong | |
| 2003/0209608 A1 | 11/2003 | Blossom | |
| 2003/0218066 A1 | 11/2003 | Fernandes et al. | |
| 2003/0226899 A1 | 12/2003 | Finkelstein | |
| 2004/0011877 A1 | 1/2004 | Reppermund | |
| 2004/0035942 A1* | 2/2004 | Silverman | 235/493 |
| 2004/0133787 A1* | 7/2004 | Doughty et al. | 713/186 |
| 2004/0159700 A1 | 8/2004 | Khan et al. | |
| 2004/0162732 A1 | 8/2004 | Rahim et al. | |
| 2004/0172535 A1 | 9/2004 | Jakobsson | |
| 2004/0177045 A1 | 9/2004 | Brown | |
| 2004/0189700 A1 | 9/2004 | Mandavilli et al. | |
| 2005/0001711 A1 | 1/2005 | Doughty et al. | |
| 2005/0043997 A1 | 2/2005 | Sahota et al. | |
| 2005/0080747 A1 | 4/2005 | Anderson et al. | |
| 2005/0086160 A1 | 4/2005 | Wong et al. | |
| 2005/0086177 A1 | 4/2005 | Anderson et al. | |
| 2005/0092830 A1 | 5/2005 | Blossom | |
| 2005/0116026 A1 | 6/2005 | Burger et al. | |
| 2005/0119940 A1 | 6/2005 | Concilio et al. | |
| 2005/0133590 A1 | 6/2005 | Rettenmyer et al. | |
| 2005/0133606 A1 | 6/2005 | Brown | |
| 2005/0154643 A1 | 7/2005 | Doan et al. | |
| 2005/0178827 A1 | 8/2005 | Shatford | |
| 2005/0194452 A1* | 9/2005 | Nordentoft et al. | 235/492 |
| 2005/0205665 A1 | 9/2005 | Lasch et al. | |
| 2005/0218229 A1 | 10/2005 | Morley et al. | |
| 2005/0219728 A1 | 10/2005 | Durbin et al. | |
| 2005/0228959 A1 | 10/2005 | D'Albore et al. | |
| 2005/0247797 A1 | 11/2005 | Ramachandran | |
| 2006/0000900 A1 | 1/2006 | Fernandes et al. | |
| 2006/0037073 A1 | 2/2006 | Juels et al. | |
| 2006/0041759 A1 | 2/2006 | Kaliski et al. | |
| 2006/0085328 A1 | 4/2006 | Cohen et al. | |
| 2006/0091223 A1 | 5/2006 | Zellner | |
| 2006/0131393 A1 | 6/2006 | Cok et al. | |
| 2006/0131410 A1 | 6/2006 | Fernandes et al. | |
| 2006/0161435 A1 | 7/2006 | Atef et al. | |
| 2006/0161789 A1 | 7/2006 | Doughty et al. | |
| 2006/0163353 A1 | 7/2006 | Moulette et al. | |
| 2006/0174104 A1 | 8/2006 | Crichton et al. | |
| 2006/0186209 A1* | 8/2006 | Narendra et al. | 235/492 |
| 2006/0196931 A1 | 9/2006 | Holtmanns et al. | |
| 2006/0249574 A1 | 11/2006 | Brown et al. | |
| 2006/0249575 A1 | 11/2006 | Turner et al. | |
| 2006/0256961 A1 | 11/2006 | Brainard et al. | |
| 2006/0261174 A1 | 11/2006 | Zellner et al. | |
| 2006/0278696 A1 | 12/2006 | Watson | |
| 2006/0278698 A1 | 12/2006 | Lovett | |
| 2006/0283958 A1* | 12/2006 | Osterweil | 235/492 |
| 2006/0287964 A1* | 12/2006 | Brown | 705/64 |
| 2007/0017975 A1 | 1/2007 | Lewis et al. | |
| 2007/0023532 A1 | 2/2007 | Narendra et al. | |
| 2007/0034700 A1* | 2/2007 | Poidomani et al. | 235/492 |
| 2007/0100754 A1 | 5/2007 | Brown | |
| 2007/0114274 A1 | 5/2007 | Gibbs et al. | |
| 2007/0124321 A1 | 5/2007 | Szydlo | |
| 2007/0131759 A1 | 6/2007 | Cox et al. | |
| 2007/0136211 A1* | 6/2007 | Brown et al. | 705/75 |
| 2007/0152070 A1 | 7/2007 | D'Albore | |
| 2007/0152072 A1 | 7/2007 | Frallicciardi et al. | |
| 2007/0153487 A1 | 7/2007 | Frallicciardi et al. | |
| 2007/0174614 A1 | 7/2007 | Duane et al. | |
| 2007/0192249 A1 | 8/2007 | Biffle et al. | |
| 2007/0241183 A1 | 10/2007 | Brown et al. | |
| 2007/0241201 A1 | 10/2007 | Brown et al. | |
| 2007/0256123 A1 | 11/2007 | Duane et al. | |
| 2007/0291753 A1 | 12/2007 | Romano | |
| 2008/0005510 A1 | 1/2008 | Sepe et al. | |
| 2008/0008315 A1 | 1/2008 | Fontana et al. | |
| 2008/0008322 A1 | 1/2008 | Fontana et al. | |
| 2008/0010675 A1 | 1/2008 | Massascusa et al. | |
| 2008/0016351 A1 | 1/2008 | Fontana et al. | |
| 2008/0019507 A1 | 1/2008 | Fontana et al. | |
| 2008/0028447 A1 | 1/2008 | O'Malley et al. | |
| 2008/0040271 A1 | 2/2008 | Hammad et al. | |
| 2008/0040276 A1 | 2/2008 | Hammad et al. | |
| 2008/0058016 A1 | 3/2008 | Di Maggio et al. | |
| 2008/0059379 A1 | 3/2008 | Ramaci et al. | |
| 2008/0093467 A1 | 4/2008 | Narendra et al. | |
| 2008/0096326 A1 | 4/2008 | Reed | |
| 2008/0099556 A1 | 5/2008 | Park | |
| 2008/0110983 A1 | 5/2008 | Ashfield | |
| 2008/0121726 A1* | 5/2008 | Brady et al. | 235/493 |
| 2008/0126260 A1 | 5/2008 | Cox et al. | |
| 2008/0126262 A1* | 5/2008 | Brady et al. | 705/75 |
| 2008/0126398 A1 | 5/2008 | Cimino | |
| 2008/0128515 A1 | 6/2008 | Di Iorio | |
| 2008/0148394 A1 | 6/2008 | Poidomani et al. | |
| 2008/0197201 A1 | 8/2008 | Manessis et al. | |
| 2008/0197533 A1 | 8/2008 | Tsao et al. | |
| 2008/0201264 A1 | 8/2008 | Brown et al. | |
| 2008/0210754 A1 | 9/2008 | Lovett | |
| 2008/0223937 A1 | 9/2008 | Preta et al. | |
| 2008/0288699 A1 | 11/2008 | Chichierchia | |
| 2008/0290166 A1 | 11/2008 | von Mueller | |
| 2008/0294930 A1 | 11/2008 | Varone et al. | |
| 2008/0302877 A1 | 12/2008 | Musella et al. | |
| 2009/0006262 A1 | 1/2009 | Brown et al. | |
| 2009/0013122 A1 | 1/2009 | Sepe et al. | |
| 2009/0036147 A1 | 2/2009 | Romano | |
| 2009/0037275 A1 | 2/2009 | Pollio | |
| 2009/0046522 A1 | 2/2009 | Sepe et al. | |
| 2009/0048971 A1 | 2/2009 | Hathaway et al. | |
| 2009/0055893 A1 | 2/2009 | Manessis et al. | |
| 2009/0108064 A1 | 4/2009 | Fernandes et al. | |
| 2009/0150295 A1 | 6/2009 | Hatch et al. | |
| 2009/0152365 A1 | 6/2009 | Li et al. | |
| 2009/0159663 A1 | 6/2009 | Mullen et al. | |
| 2009/0159667 A1 | 6/2009 | Mullen et al. | |
| 2009/0159696 A1* | 6/2009 | Mullen | 235/493 |
| 2009/0159702 A1* | 6/2009 | Mullen | 235/493 |
| 2009/0159709 A1* | 6/2009 | Mullen | 235/493 |
| 2009/0164380 A1 | 6/2009 | Brown | |
| 2009/0164381 A1 | 6/2009 | Brown | |
| 2009/0187507 A1 | 7/2009 | Brown | |
| 2009/0255996 A1 | 10/2009 | Brown et al. | |
| 2009/0261161 A1 | 10/2009 | Blossom | |
| 2010/0084476 A1 | 4/2010 | Zellner et al. | |
| 2010/0127083 A1 | 5/2010 | Brown et al. | |
| 2010/0127830 A1 | 5/2010 | Nielsen et al. | |
| 2010/0265037 A1 | 10/2010 | Domsten et al. | |
| 2010/0270373 A1* | 10/2010 | Poidomani et al. | 235/380 |
| 2011/0006122 A1* | 1/2011 | Chenot | 235/493 |
| 2011/0028184 A1 | 2/2011 | Cooper | |
| 2011/0174874 A1* | 7/2011 | Poznansky et al. | 235/379 |

| | | | | |
|---|---|---|---|---|
| 2011/0220726 | A1* | 9/2011 | Narendra et al. | 235/492 |
| 2011/0272472 | A1* | 11/2011 | Mullen | 235/492 |
| 2011/0272476 | A1 | 11/2011 | Mullen et al. | |
| 2011/0272479 | A1* | 11/2011 | Mullen | 235/492 |
| 2012/0191612 | A1* | 7/2012 | Spodak et al. | 705/65 |

FOREIGN PATENT DOCUMENTS

| | | |
|---|---|---|
| GB | 2420098 | 5/2006 |
| JP | 05210770 A | 8/1993 |
| WO | WO9852735 | 11/1998 |
| WO | WO0247019 | 6/2002 |
| WO | WO2006066322 | 6/2006 |
| WO | WO2006080929 | 8/2006 |
| WO | WO2006105092 | 10/2006 |
| WO | WO2006116772 | 11/2006 |
| WO | WO2007141779 | 12/2007 |

OTHER PUBLICATIONS

U.S. Appl. No. 60/675,388, Poidomani et al.

The Bank Credit Card Business. Second Edition, American Bankers Association, Washington, D.C., 1996.

A Day in the Life of a Flux Reversal. http://www.phrack/org/issues.html?issue=37&id=6#article. As viewed on Apr. 12, 2010.

Dynamic Virtual Credit Card Numbers. http://homes.cerias.purdue.edu/~jtli/paper/fc07.pdf. As viewed on Apr. 12, 2010.

USPTO, International Search Report, Apr. 28, 2009.

English translation of JP 05210770 A.

EPO, Extended European Search Report, Jan. 26, 2012.

* cited by examiner

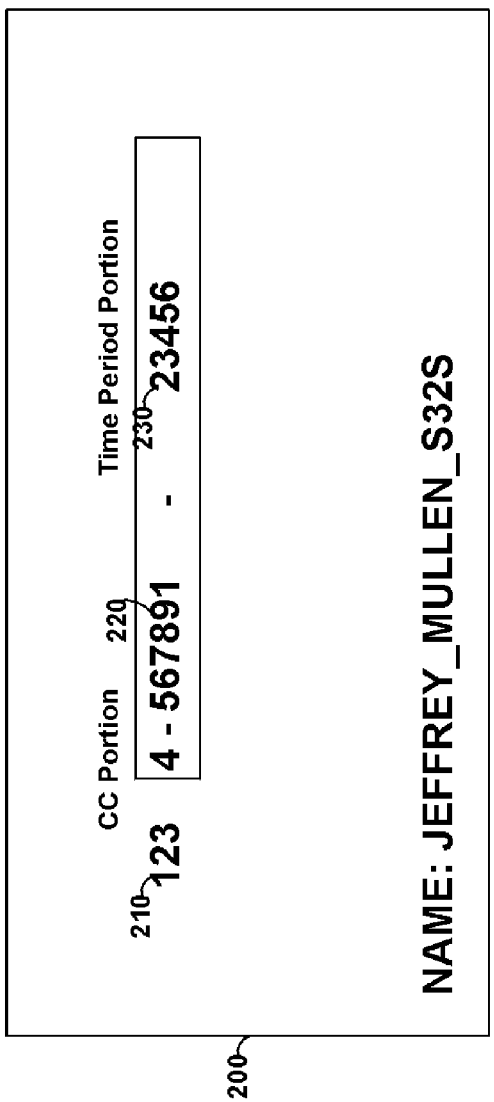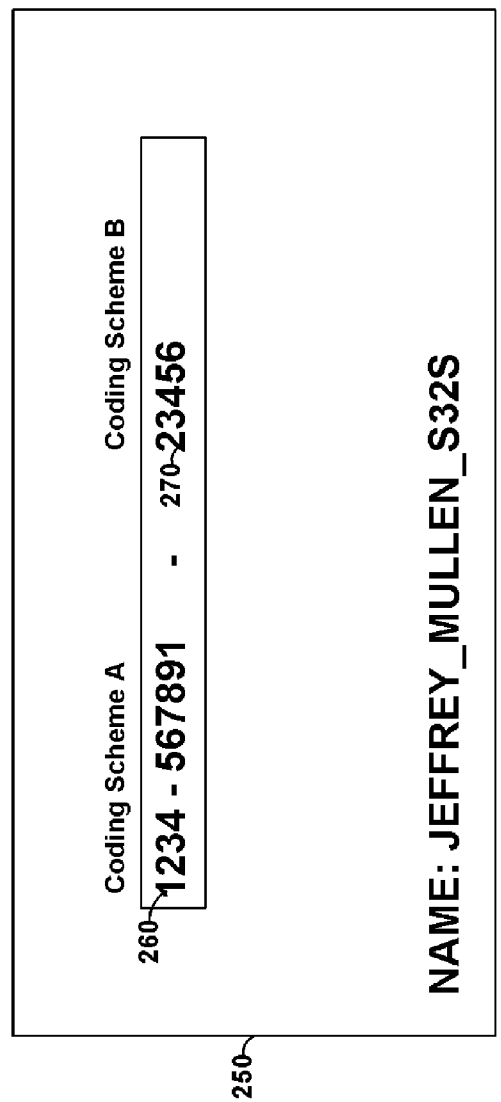
FIG. 2

ADVANCED DYNAMIC CREDIT CARDS

CROSS-REFERENCE TO RELATED APPLICATIONS

This application is a continuation of U.S. patent application Ser. No. 12/339,065, filed on Dec. 19, 2008, which claims the benefit of U.S. Provisional Patent Application Nos. 61/016,491 filed on Dec. 24, 2007, 61/026,846 filed on Feb. 7, 2008, 61/027,807 filed on Feb. 11, 2008, 61/081,003 filed on Jul. 15, 2008, 61/086,239 filed on Aug. 5, 2008, 61/090,423 filed on Aug. 20, 2008 61/097,401 filed Sep. 16, 2008, 61/112,766 filed on Nov. 9, 2008, 61/117,186 filed on Nov. 23, 2008, 61/119,366 filed on Dec. 2, 2008, and 61/120,813 filed on Dec. 8, 2008, all of which are hereby incorporated by reference herein in their entirety.

BACKGROUND OF THE INVENTION

This invention relates to payment cards such as credit cards.

SUMMARY OF THE INVENTION

A card is provided with a dynamic number. For example, a payment card, such as credit card, is provided with a dynamic payment card number, such as a dynamic credit card number. A dynamic credit card number may, for example, change based on time or use.

A portion of a dynamic credit card number may be static. Accordingly, for example, the credit card number may change but particular digits of the dynamic credit card number may remain constant. For example, a dynamic credit card number may be provided such that the beginning one or more digits (e.g., first six digits) are static.

As such, the beginning one or more digits of a number may be representative of the type of card (e.g., a dynamic credit card) as well as other information. Such information may include, for example, routing information such that at least some of the digits of a number may be communicated to remote servers according to the static routing information.

For example, the beginning digit of numerous dynamic credit cards may have the same static one or more digits (e.g., beginning digits). For example, the beginning digits of an American Express dynamic credit card may take the form of "399." The first digit (e.g., "3") may be representative of the card manufacturer (e.g., "American Express"). The second and third digits (e.g., "99") may be representative of the type of card (e.g., a dynamic credit card).

A magnetic emulator may be provided on a card (e.g., a credit or debit card). Such a magnetic emulator may include one or more wires that are able to produce an electromagnetic field that is operable to be read by, for example, a magnetic stripe reader. The magnetic emulator may be provided about a magnetic stripe and may be utilized to produce an electromagnetic field such that, for example, a magnetic stripe reader may seamlessly read a portion of the magnetic stripe, then read fields generated from the magnetic emulator, then read another portion of the magnetic stripe. In doing so, for example, only particular information related to an account (e.g., all or a portion of a credit card number) may be communicated via a magnetic emulator and, as such, may be operable to be changed.

A magnetic emulator may be placed adjacent to a magnetic stripe such that the first data read by a magnetic stripe data is provided by the magnetic emulator. Similarly, numerous magnetic emulators may be provided about one or more magnetic stripes. For example, a magnetic emulator may be provided at different locations on different tracks of a magnetic stripe. Magnetic emulators may share, for example, similar control circuitry. Magnetic emulators may communicate data directly to a read-head of a card reader without the presence of a magnetic medium. A card may be provided with one or more emulators and without a magnetic stripe.

A magnetic encoder may be provided, for example, to change the state of magnetic filaments located on a magnetic stripe such that information may be changed. A magnetic encoder may write information on a magnetic material configured for that magnetic encoder. Accordingly, for example, a card (e.g., a security card) may be provided with a magnetic stripe having one set of attributes (e.g., one coercivity) and another magnetic stripe, configured for use with a magnetic encoder, having a different set of attributes (e.g., a different coercivity).

An identification name may be printed on the front of a card (e.g., a credit, debit, or security card). This name may be unique. Accordingly, for example, no two credit cards may be fabricated that utilize the same identification name. For example, instead of providing a card with an identification name of "Christopher Mullen," that card may include an identification name of "Christopher-Mullen-201." As such, a user on a website may utilize the identification name in a field representative of "name on card"/"name of account holder." Such an identification name may also be communicated to a magnetic stripe reader via a magnetic stripe or magnetic emulator located on a credit card.

A batch of credit card numbers may be partitioned such that, for example, two users having the same name may not, for example, have a dynamic credit card associated with the same particular partition. For example, suppose the first three numbers of a dynamic credit card number are static (e.g. "391"). The first digit (e.g., "3") may be representative of a credit card manufacturer (e.g., "American Express."). The second digit (e.g., "9") may be representative of the type of credit card (e.g., a dynamic credit card). The third digit (e.g., "1") may be representative of the partition. Accordingly, a credit card verification process may be able to recognize a partition. Using this scheme, for example, ten partitions may be provided (e.g., "390-399"). As such, ten people using the exact same name may be provided with a dynamic credit card that utilizes this scheme and each could be provided with a different partition.

More than one display may be utilized on a card, such as an identification card or credit card. A single controller (e.g., a processor) and a clock may be utilized to drive such displays. Similarly, each display may be provided with its own controller and clock. The clock may supply timing signals to such controllers. Accordingly, each controller may be provided with a different type of coding. For example, one controller may utilize one coding scheme and another controller may utilize another coding scheme. As such a dynamic number, such as a dynamic credit card number, may be provided by one or more displays run by different coding schemes. If one coding scheme is compromised by a thief, such an additional coding scheme would provide additional security. Similarly, a single controller may provide multiple coding schemes to different portions of a dynamic number (e.g., a dynamic credit or debit card number).

A dynamic number may change periodically. A dynamic number may change based on a time period. This time period may be displayed on a display. For example, the time period may be a portion of a dynamic number. Accordingly, a transmitted dynamic number may include the information as to what time period, or time periods, the dynamic number is associated with.

A dynamic code may be provided. A dynamic code may be provided on its own display or on a display providing other information (e.g., dynamic card number). Such a dynamic code may be, for example, a dynamic security code. Accordingly, for example, a dynamic security code may be utilized with a dynamic card number to authorize a payment transaction. Such a dynamic code may also be communicated through a magnetic emulator or encoder. Alternatively, for example, one dynamic code may be communicated visually (e.g., for online transactions) and a different dynamic code may be communicated magnetically (e.g., for in-store transactions). Such codes may change based on time or use. One or more buttons may be provided to change a particular dynamic number or all dynamic numbers. For example, a button may be utilized to change a dynamic card number and a different button may be utilized to change a dynamic security code for online use. A single button may be provided, for example, that changes all dynamic numbers (e.g., a card number provided on a display, an online security code provided on the same or a different display, and an in-store code communicated magnetically to a magnetic stripe reader). An in-store code and an online security code may be, for example, the same code. Different tracks of data may, for example, have different security codes.

BRIEF DESCRIPTION OF THE DRAWINGS

The principles and advantages of the present invention can be more clearly understood from the following detailed description considered in conjunction with the following drawings, in which the same reference numerals denote the same structural elements throughout, and in which:

FIG. 2 is an illustration of cards constructed in accordance with the principles of the present invention;

DETAILED DESCRIPTION OF THE INVENTION

Figure 1:
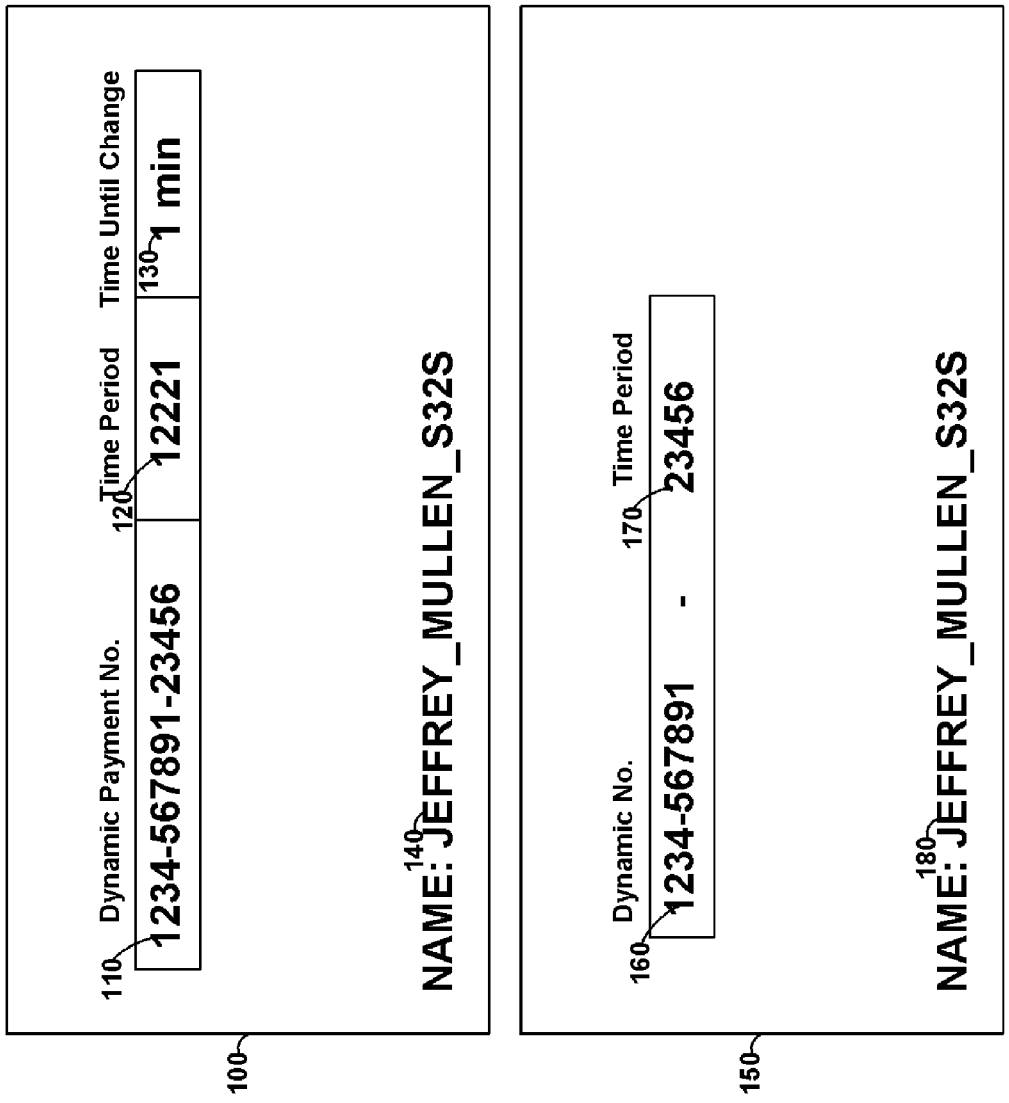
FIG. 1 is an illustration of cards constructed in accordance with the principles of the present invention.

FIG. 1 shows card 100 that may include a display that displays dynamic credit card number 110, time period 120, and time until change information 130.

Identification information 140 may also be included on card 100. Identification information 140 may be permanently provided on card 100 or may be displayed on a display (e.g., the display that displays dynamic credit card number 110). For example, identification information 140 may be printed onto card 100 or embossed on card 100.

Dynamic credit card number 110 may be changed periodically. Additionally, a number may be changed right after a user enters a number into an online checkout process—but before that online checkout process completes. Accordingly, a particular number of dynamic credit card number 110 may, for example, be valid during time period 120 in which the particular number was generated. Dynamic numbers may, or may not, be repeated. The numbers that are valid for a particular period of time may be, for example, a numbers generated in adjacent time slots (e.g., the time slot or time slots before and after the generation of the displayed number).

A display may be bi-stable or non bi-stable. A bi-stable display may consume electrical energy to change the information displayed on the bi-stable display but may not consume electrical energy to maintain the display of that information. A non bi-stable display may consume electrical energy to both change and maintain information on the non bi-stable display. A display driving circuit may be provided, for example, for a bi-stable display (or a non bi-stable display). Such a display driving circuit may step-up a supply voltage (e.g., 1-5 volts) to a larger voltage (e.g., 6-15 volts) such that a bi-stable display may change displayed information. A controller (e.g., a processor) may be utilized to control such a display driving circuit.

Persons skilled in the art will appreciate that a particular number may be verified by a verification system (e.g., a credit card verification server) during a time period not associated with the particular number. In such instances, for example, the particular number may be transmitted along with the time period in which the particular number was generated. Accordingly, the particular number may be verified as being generated during the time period by the verification server. In instances of fraud, the cost of fraud may be transferred to the entity that provided the particular number and time period. In this manner, the liability for fraud may be transmitted to the entity that stores the particular number and time period for later use. In doing so, entities may be encouraged to, for example, only transmit current dynamic credit card numbers. The cost of fraud may be transferred, for example, to the association or bank that issued the card.

A website may include, for example, a text box that would allow a user to provide timing information 120. A different coding scheme may also be associated with each, or with a group of, different time periods. A credit card verification system may include a timing circuit that is in sync with a timing circuit on card 100 such that both the verification system and card 100 are aware of the current time period of card 100. A time period may be, for example, on the order of minutes, hours, or days. For example, a time period may be approximately 36 hours in duration.

Time until change information 130 may be provided on a display and may be representative of the amount of time remaining before number 110 changes.

Identification information 140 may be provided on card 100. Identification information 140 may be provided such that each card 100 has different identification information 140. Accordingly, even though to users may have the same name, each user may have different identification information 140. In doing so, a user may enter in identification information 140 on a text box at an online store and a verification system may, for example, be able to identify a particular user based on identification information 140. A number may include one or more digits representative of information that may be utilized in an identification process. For example, two digits may be representative of a partition. Users having the same name may be assigned different partitions. Accordingly, the name on a card may be associated with the name of a person. People with the same name may have the same identification information. However, such people with the same name may be recognized by having different identification digits. Two identification digits in a credit card number may allow for 100 partitions. Similarly, identification information may be provided in a dynamic credit card number. The digits for identification may change location each period or particular groups of periods as well as may be coded differently each period or particular groups of periods. Identification digits may be static (e.g., printed on a credit card or statically displayed so the digits do not change). In printing a static number of a card, for example, the amount of power needed to display a credit card number may be reduced.

Persons skilled in the art will appreciate, for example, that at least the first six digits of payment card number may remain static and may be utilized to route at least the rest of the payment card number to the appropriate verification network. Portions of remaining digits may remain static and may be utilized for identification while other remaining digits may be dynamic.

Card 150 may be provided and may include a display that includes a dynamic number with portion 160 that corresponds to a credit card number and portion 170 that corresponds to a time period. Persons skilled in the art will appreciate that other portions may be provided in such a number or that a particular portion may include particular information. For example, user identification information may be utilized as part of portion 160. Persons skilled in the art will appreciate that a static number may be permanently provided on a card (e.g., via printing or embossing). Alternatively, for example, a display may display a particular digit or digits time the display displays a card number. Persons skilled in the art will appreciate that a display may be configured to display numerical data or alphanumerical data. A display may also be configured to display other indicia (e.g., the image of a battery and its remaining life).

Persons skilled in the art will appreciate that portions 160 and 170 may take the form of a credit card number (e.g., a fifteen digit number that is transmitted as a credit card number to a credit card verification server). Additionally, any digit or digits of a dynamic credit card number may be static. For example, at least the first digit may be static. In doing so, for example, a credit card verification system may be able to identify a credit card number as being a dynamic credit card number.

A credit card number with three digits allocated for a time period associated with the generated number may, for example, be sufficient to provide enough time periods for a card's life. For example, suppose a time period is associated with a day. Three digits would provide for 1000 days of operation. As a card may be provided with a magnetic emulator or magnetic stripe encoder, additional information may be transmitted to a card verification system. For example, user identification information and time period information not embodied as a credit card number may be transmitted to a remote credit card verification system via a local magnetic stripe reader.

FIG. 2 shows card 200 that includes a credit card number having static portion 210, displayed portion 220, and displayed portion 230. Static portion 123 may be utilized such that a credit card verification system is able to recognize that a credit card number is a dynamic credit card such as an American Express dynamic credit card. Portion 220 may be dynamic and may periodically change. In doing so, the amount of fraud associated with card number theft may be reduced. Portion 230 may be representative of a time period for portion 220. Accordingly, identification of a number being a dynamic card number, a time stamp, and a dynamic number may all be transmitted as a 15-digit credit card number. Persons skilled in the art will appreciate that a payment card number may have different lengths. For example, a payment card number may be 19 digits in length or 16 digits in length. Persons skilled in the art will appreciate that a time period, for example, does not have to be transmitted. Systems may, for example, assume that a card is synchronized to a verification server. Similarly, transmission of a time stamp may be optional. As such, for example, a time stamp may be transmitted when one-click shopping is utilized by a particular online store, but a time stamp may not be needed, for example, when a purchase is made and a credit card number is entered for immediate processing.

Card 250 includes a number, which may be utilized as a credit card number, which includes portion 260 and 270. Portion 260 may include, for example digits that may be representative of the type of number displayed (e.g., a dynamic credit card number). Portion 260 may also include a dynamic number that may be utilized by a credit card processing system to a make a purchase on credit. Portion 270 may, for example, include digits associated with a time period for a dynamic credit card number. Portions 260 and 270 may be coded by different coding procedures. Accordingly, if the integrity of one procedure is compromised, a dynamic credit card may still provide security if, for example, the integrity of the other coding procedure is still intact.

Figure 3:
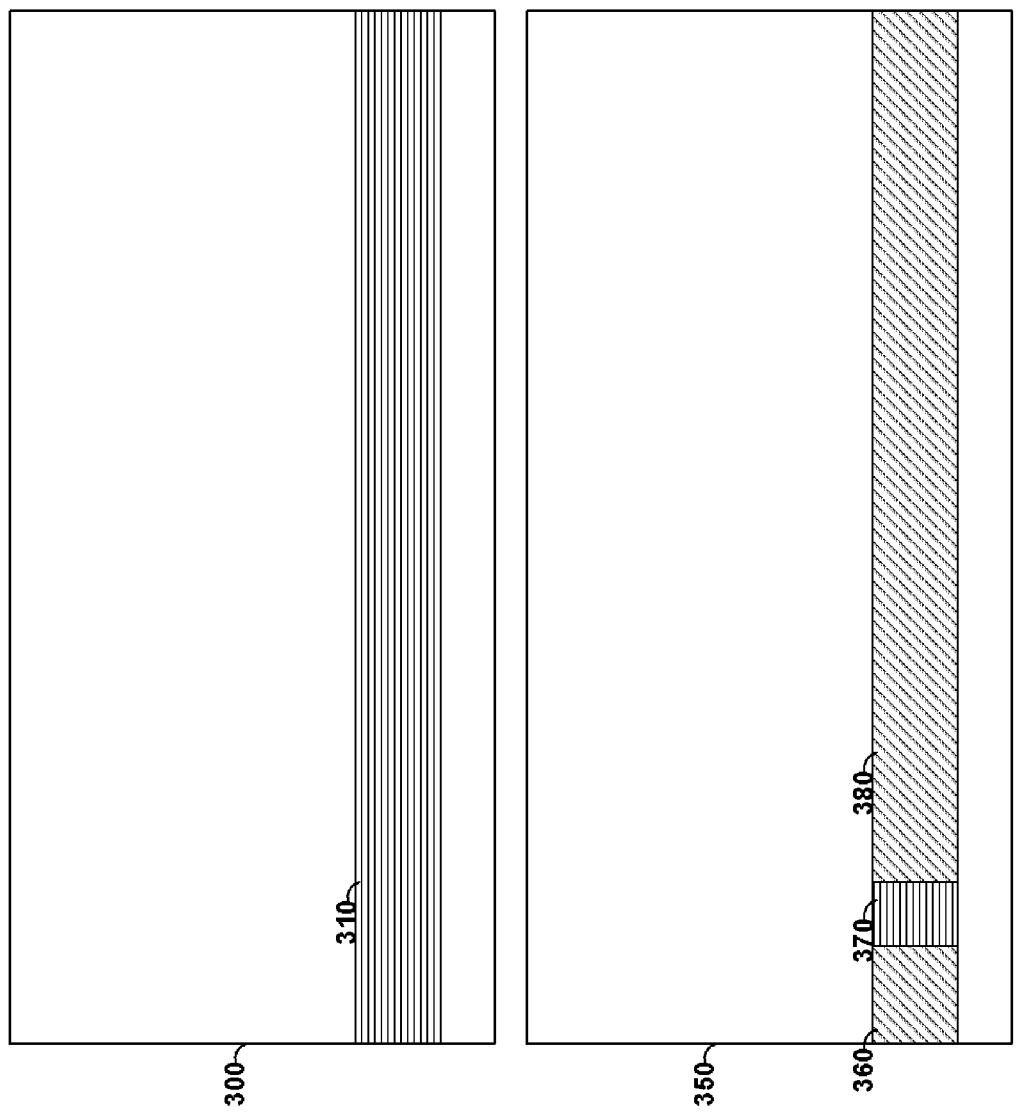
FIG. 3 is an illustration of cards constructed in accordance with the principles of the present invention.

FIG. 3 shows credit card 300 may include structure 310 which may be, for example, a dynamic magnetic communications device such as a magnetic stripe encoder or a magnetic emulator. A magnetic stripe encoder may, for example, erase and re-write information to a magnetic stripe. A magnetic emulator may, for example, generate electromagnetic fields that are able to be read by a magnetic stripe reader.

Persons skilled in the art will appreciate that a button may be included that may provide a variety of capabilities. For example, a button, when pressed, may cause a magnetic stripe encoder to write a number (e.g., the credit card number generated at the time the button is pressed) to the magnetic stripe. This number may also be displayed on a display. As per another example, a button, while pressed, may cause a magnetic emulator to turn ON and emulate fields. A magnetic emulator or encoder may comprise a number of wires. A current may be flowed through the wires at particular strengths and polarities to generate fields capable of, for example, writing to a magnetic stripe or being read by a magnetic stripe reader.

Card 350 may include magnetic stripe portions 360 and 380 as well as magnetic encoder or emulator 370. Persons skilled in the art will appreciate that only a particular portion of information that needs to be transmitted may need to change. Accordingly, a dynamic encoder or emulator does not, for example, need to be utilized to emulate or encode all of the transmitted information. An encoder and/or emulator may be utilized, for example, to communicate a dynamic credit card number or a portion of a dynamic credit card number to a credit card reader. Similarly, an encoder and/or emulator may be utilized, for example to communicate a time period, dynamic feedback (e.g., whether the battery is LOW or the card has been breached by a thief), or identification information.

A rechargeable battery may be provided such that, for example, the card may be inserted into a device capable of recharging the rechargeable battery.

A magnetic credit card stripe may have multiple tracks. One or more magnetic encoders and/or emulators may be utilized to communicate information on one or more (e.g., all) tracks). Persons skilled in the art will appreciate that different tracks may be provided with a different bit density (e.g., bits-per-inch). Accordingly, the spacing of wires on emulators/encoders may be different depending on the type of track the emulator/encoder is attempting to emulate/encode.

An encoder and/or emulator may be placed adjacent to a magnetic stripe or underneath a magnetic stripe. For example, a particular portion of a particular track may be cut-out from a multiple track magnetic stripe and an emulator may be placed in this cut-out portion on a card. A magnetic encoder and/or emulator may be placed, for example, before a magnetic stripe, after a magnetic stripe, or with a magnetic stripe.

Figure 4:
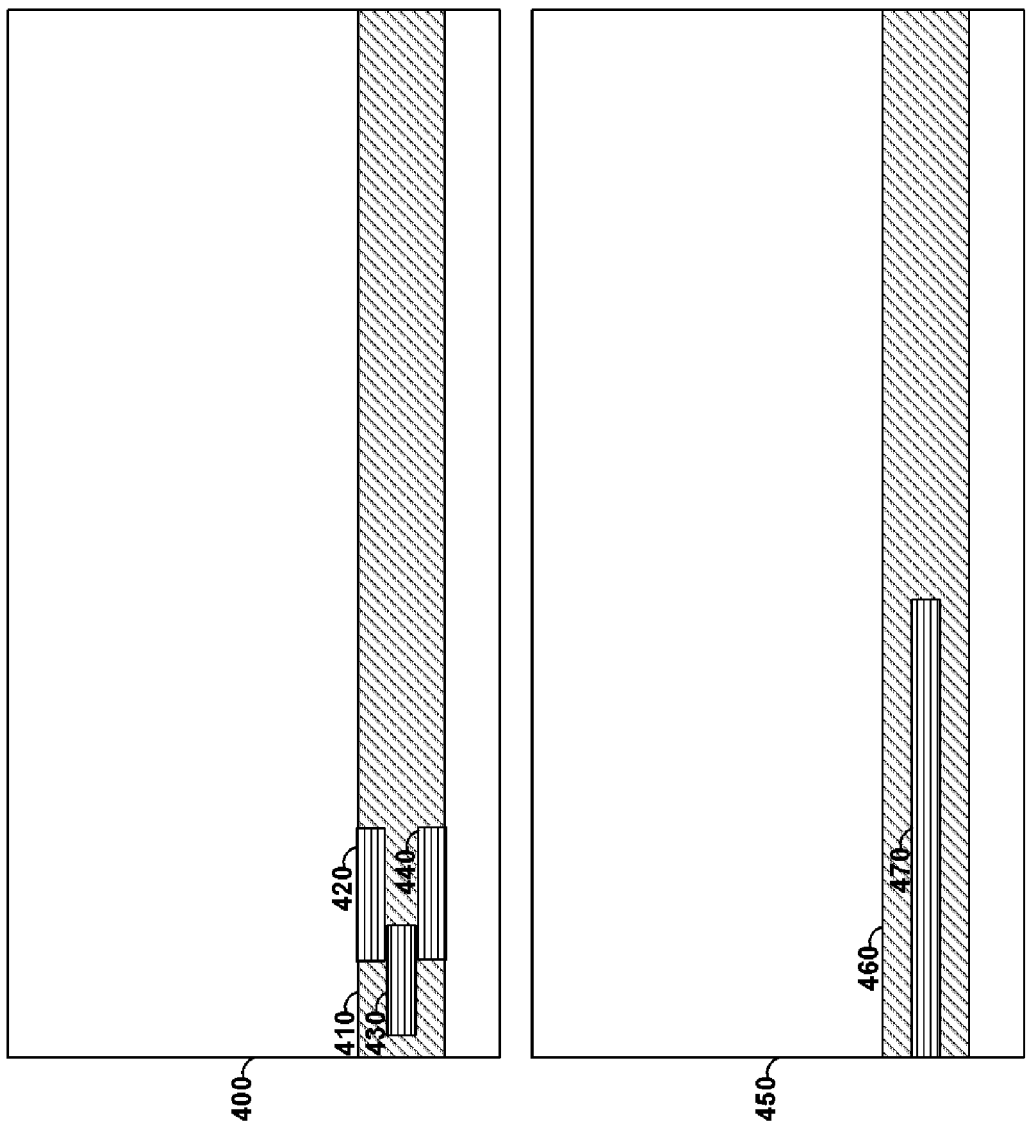
FIG. 4 is an illustration of cards constructed in accordance with the principles of the present invention.

FIG. 4 shows card 400 that may include magnetic stripe 410, magnetic emulator 420, magnetic emulator 430, and magnetic emulator 440. Magnetic emulators 420, 430, and 440 may, for example, be utilized to emulate similar information, but on different tracks of a multiple track magnetic stripe. Similarly, magnetic emulators 420, 430, and 440 may be placed on different horizontal portions of their respective tracks so that each emulator provides similar information on each track. For example, suppose that a middle track includes a higher bit density then exterior tracks (e.g., in a three-track embodiment). Then, for example, magnetic emulator 430 may be located in a different location then emulators 420 and 440. Similarly, the two exterior tracks in a three-track magnetic stripe may be have a higher bit density then a middle track. Additionally, for example, different tracks may have data formatted in different ways. Accordingly, similar information on each track may be located in different areas due to formatting.

The exterior tracks in a three-track configuration (e.g., tracks 1 and 3) may, for example, be provided at 210 bits per inch. The middle track in such a configuration (e.g., track 2) may be provided at 75 bits per inch. Persons skilled in the art will appreciate that, for example, a magnetic stripe encoder may be utilized instead of a magnetic emulator. Magnetic stripe encoders may, for example, be placed under a portion of a magnetic stripe. Persons skilled in the art will appreciate that a payment card may be provided with any number of tracks. For example, a payment card may be provided with two tracks (e.g., tracks 1 and 2). Different tracks may include similar data (e.g., card numbers) as well as different data. For example, one track (e.g., track 1, which may be the track closest to the bottom of the card) may include name information while another track (e.g., track 2, which may be located above track 1).

Card 450 may include magnetic stripe 460 and magnetic encoder and/or emulator 470. Magnetic stripe 460 may have three tracks of data. As such, card 450 may include multiple tracks (e.g., three) and magnetic encoder and/or emulator 470 may, for example, form a portion of one of these tracks. The rest of the tracks may, for example, be provided as a magnetic stripe without a magnetic encoder/emulator. A single track may include, for example, any number of magnetic emulators and/or magnetic encoders.

For example, a single track may include a magnetic emulator (or encoder) at the beginning and end of a track such that the middle of the track is provided by a magnetic stripe. Similarly, a single track may include a magnetic emulator (or encoder) at, for example, just the beginning of a track. Similarly still, a single track may include a magnetic emulator (or encoder) at, for example, just the end of a track. A magnetic encoder or emulator located at an end of a magnetic stripe may, for example, communicate a string of a particular bit (e.g., zeros) to aid a magnetic reader's reading of magnetic stripe information. A magnetic stripe reader may be configured to, for example, determine the rate at which bits are being communicated by looking at a string of zeros provided on a card before, and after, payment card information. Persons skilled in the art will appreciate that a card may provide magnetic stripe information either in a forward configuration or backwards configuration. For example, a magnetic emulator, or encoder, may provide payment information in reverse order. Accordingly, a payment number may be communicated in payment information from its least significant digit to its most significant digit instead of from, for example, its most significant digit to its least significant digit. Persons skilled in the art will appreciate that magnetic stripe data may, for example, be provided as characters. Numerical data may be, accordingly, described in such magnetic stripe data as characters. In such instances, for example, a particular character of data may be utilized to just describe numerical data. Routing servers may, for example, look for such numerical data. Persons skilled in the art will appreciate that additional states may be provided in characters that are not used. Such additional states may be utilized to communicate, for example, additional information while still communicating numerical data. For example, a character that includes twenty or more states may be utilized to describe a digit as well as an extra bit of data. The first and eleventh character may correspond, for example, to the same digit (e.g., "0"). However, for example, the selection of the first and eleventh states may be utilized to transmit additional information. Such additional information may be, for example, a piece of the timing information or information indicative of a coding scheme used. Accordingly, a remote server (e.g., a routing or verification server) may be able to extract both digit information as well as additional information for a character associated with a digit under a particular data structure (e.g., an American Express credit card number format) and communicate these pieces of data to another server or different servers. The inclusion of additional data may be provided, for example, for any character of a data structure that has a number of states greater than the number of states used to describe its corresponding information under that structure. Different tracks of data may include, for example, different types of characters that utilize a different number of states. For example, a track (e.g., track 1) may include 7-bit characters while a different track (e.g., track 2) may include 5-bit characters. Characters as well as tracks of data may include, for example parity bits as well as different types of sentinels (e.g., start and end sentinels). A track of data may be provided with a character for a Longitudal Redundancy Check (LRC). A processor may encrypt, for example, entire tracks of data based on time or use. A processor may encrypt, for example, one or all tracks of data provided on a card.

Figure 5:
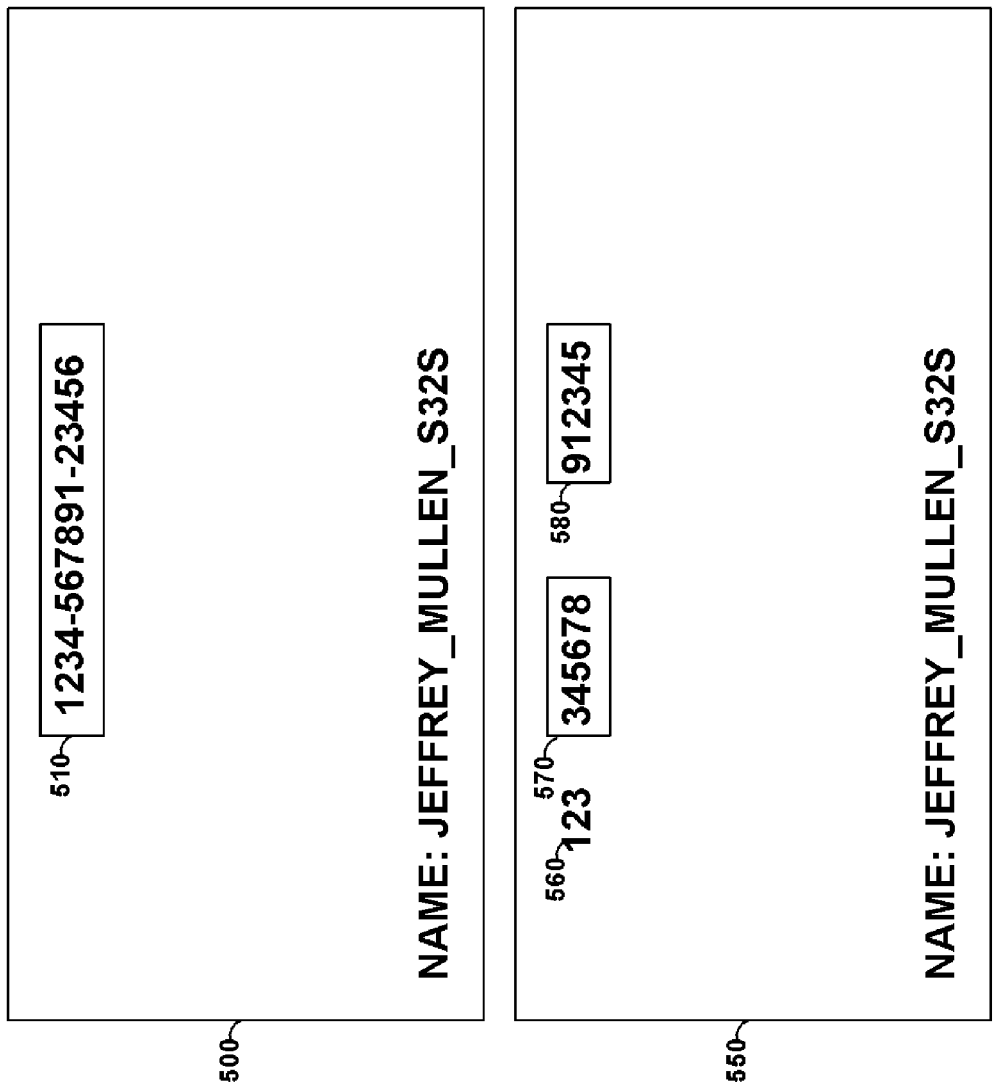
FIG. 5 is an illustration of cards constructed in accordance with the principles of the present invention.

FIG. 5 shows card 500 that includes display 510. Display 510 may, for example, be located near the top of a card 500. Display 510 may also be, for example, provided in the middle of the top of card 500 or off-set from the middle of card 500 (e.g., either left or right of the middle). In doing so, for example, the amount of space beneath the display may be maximized. Accordingly, the size of particular components may be increased. For example, a battery may be placed beneath display 510 and the location of a display at the top of card 500 may allow for a battery of increased size. By increasing the size of a battery, the life of card 500, without a recharge, may be increased. One or more batteries may be utilized in card 500.

Card 550 may include display 570 and 580 that may provide part of a credit card number. Static information 560 may also be utilized as part of that credit card number. Displays 570 and 580 may each be operated by a different microprocessor. Each of displays 570 and 580 may operate under different coding procedures (provided by the different processors). A single processor may be utilized to provide the different coding procedures. Displays 570 and 580, and the associated processors, may be clocked by a single clock and may be powered by a single battery. Persons skilled in the art will appreciate that any number of processors, clocks, or any other structure may be utilized in card 550. Displays 570 and 580 may, for example, be located near the top of card 550.

Persons skilled in the art will appreciate that any information utilized in any type of payment transaction (e.g., credit card transaction) may be displayed on a display and communicated to a reader via an emulator or encoder. For example, a user's zip code may be provided on a dynamic credit card on a display as a dynamic number that changes with time. This zip code may be representative of, for example, a time stamp. In this manner, for example, a user may communicate a time stamp to a credit card verification system by entering in the dynamic time stamp into a text box located on the payment stage of an online store.

Persons skilled in the art will also appreciate that a fifteen digit number may be sufficient to provide a large amount of data. For example, a first portion of digits may identify a credit card as a dynamic credit card (e.g., digits 1 and 2). A second portion may identify a user (e.g., digits 3-9). A third portion may be representative of a security code that changes with respect to time (e.g., digits 10-13). A fourth portion may be representative of a time-stamp (e.g., digits 14 and 15). Any portion (e.g., the first portion and second portion) may be static and, as such, may be printed on a credit card. A time stamp may, for example, cycle through and restart at 0. Accordingly, for example, a two digit time stamp may start at 00, end at 99, and then restart at 00. If such a time stamp changes every day, the chances that a time-stamp is not synchronized with a server may be relatively low. Persons skilled in the art will appreciate that environmental characteristics such as temperature may affect the operation of a clock and may introduce delay. Accordingly, the time stamp may be utilized, for example, to confirm that the credit card is in synchronization with a verification system.

Figure 6:
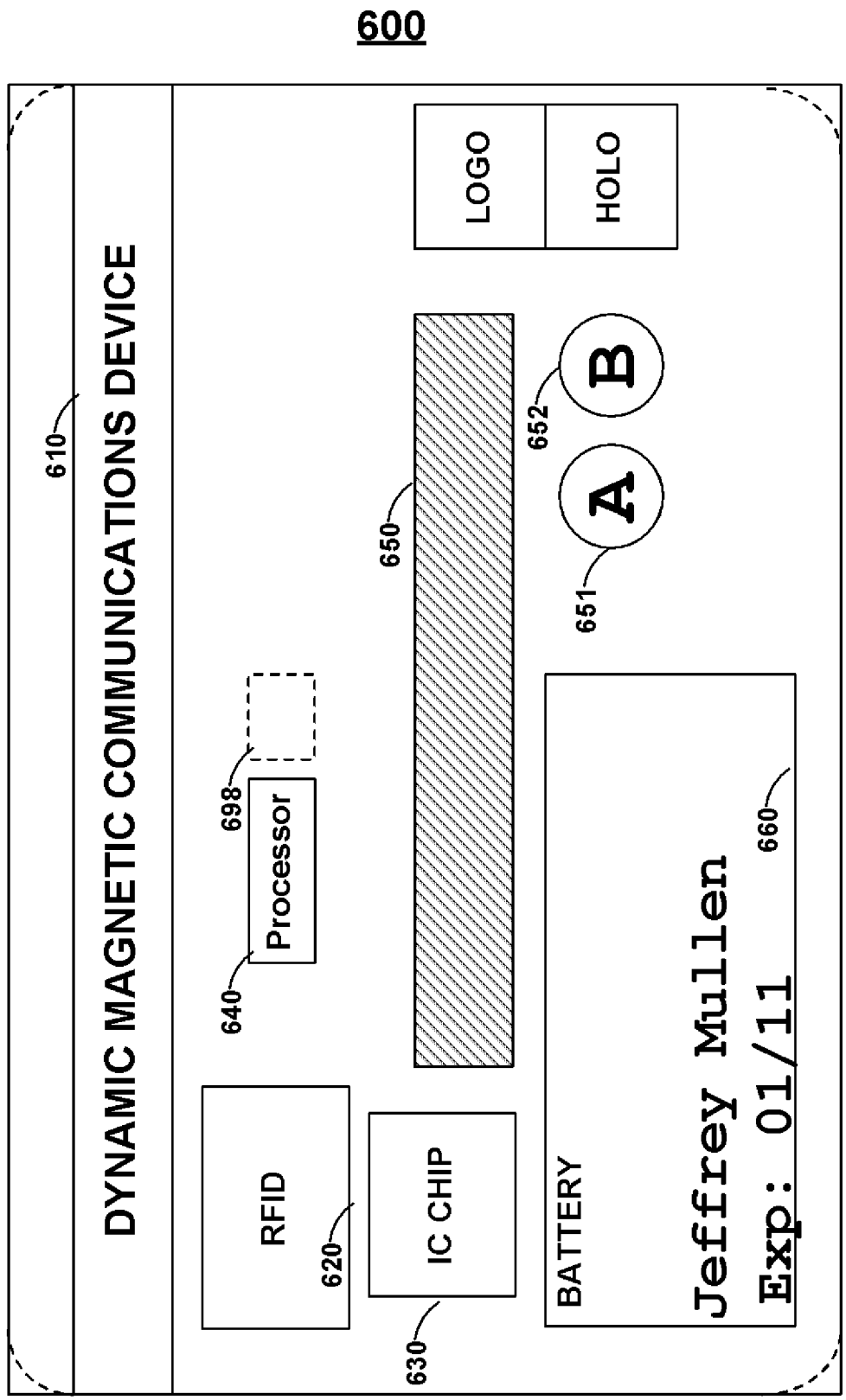
FIG. 6 is an illustration of a card constructed in accordance with the principles of the present invention.

FIG. 6 shows card 600 that may include, for example, one or more IC chips 630 (e.g., EMV chips), RFID antennas 620, processors 640, displays 650, dynamic magnetic communications devices 610 (e.g., magnetic encoders and/or magnetic emulators), batteries 660, and buttons 651 and 652. Additionally circuitry 698 may be provided and may include, for example, one or more oscillators or additional circuitry. Persons skilled in the art will appreciate that button 651 may, for example, be utilized by a user to select one encryption algorithm for a number displayed on display 650 while button 652 may be utilized by a user to select a different encryption algorithm. Persons skilled in the art will appreciate that the components of card 600 may be provided on either surface of a card (e.g., a front or rear surface of the card) or inside of a card. A logo (e.g., of a card issuer) and logo may be provided on either surface of a card.

A button, such as button 651, may be utilized, for example, to display a number. Such a number may be, for example, encrypted from a secure number based on time or use. For example, one-time use numbers (e.g., a payment number or code) may be retrieved from a list of numbers on memory each time button 651 is pressed and displayed on display 650. A processor may only go through each number once on a list. A registration process may be provided in which a user may be requested to enter in a sequence of numbers such that a remote server may validate the card and learn where in a sequence of a list a card currently resides. Numbers may be repeated on a list or may only occur once on a list. All of the numbers available by the length of the number may be utilized by the list or only a portion of the numbers available by the length of the number may be provided by the list. A secret number may be encrypted on a card and a verification server may also have knowledge of this secret number. Accordingly, the remote server may perform the same encryption function as the card on the secret number and verify that the resultant encrypted number is the same as the resultant encrypted number on a card. Alternatively, for example, the remote server may decrypt the received encrypted number to determine the authenticity of the encrypted number and validate an activity (e.g., validate a security access request or a purchase transaction).

Figure 7:
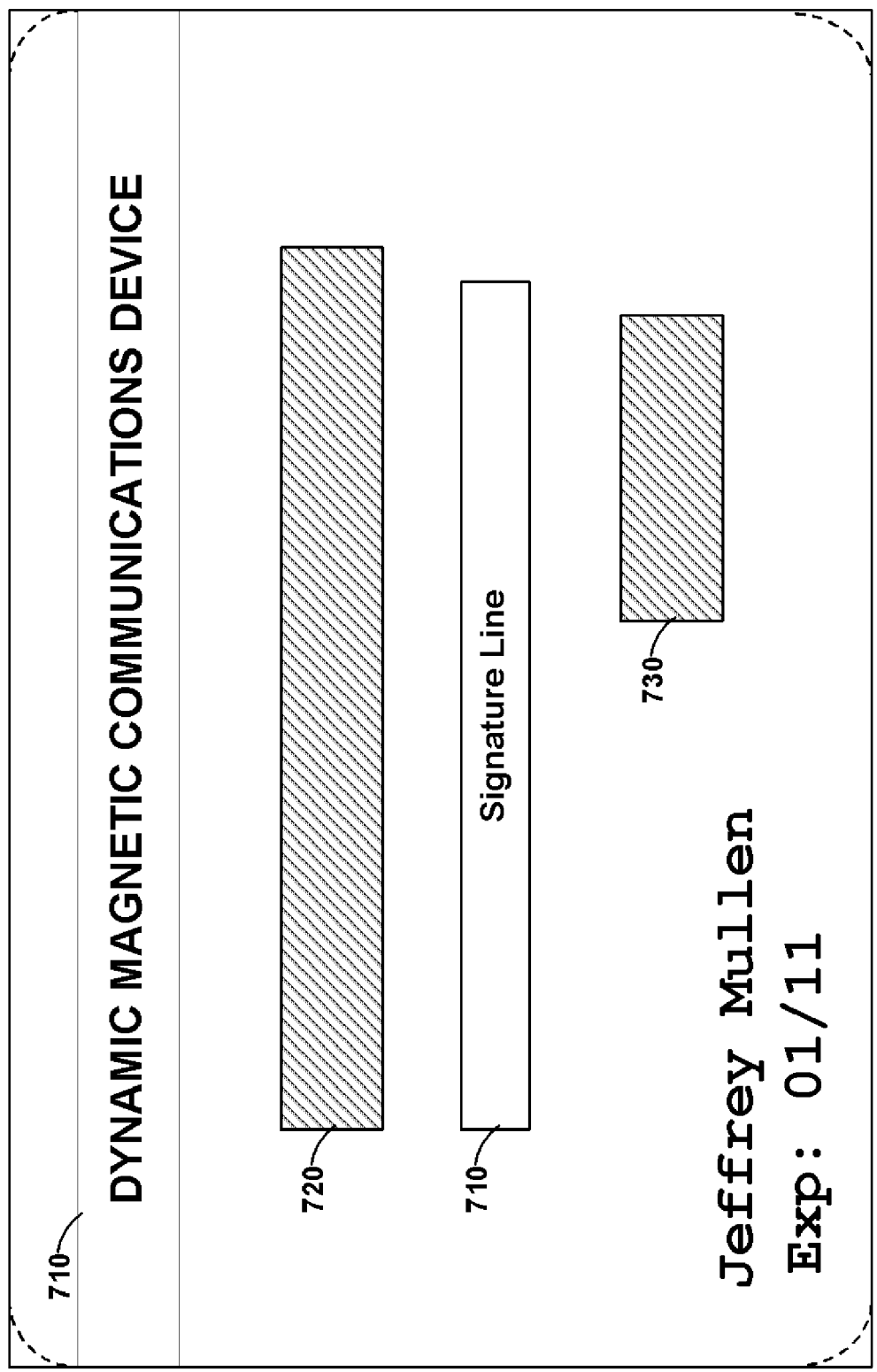
FIG. 7 is an illustration of a card constructed in accordance with the principles of the present invention.

FIG. 7 shows card 700 that may include, for example, signature area 710 that may include a material operable to receive marks from a pen (e.g., a signature). Card 700 may also include, for example, displays 720 and 730. Display 720 may, for example, display a payment number while display 730 displays a security code (e.g., for online purchase authentication). Display 720 as well as display 730 may be utilized on the same side as, for example, dynamic magnetic communications device 710.

Figure 8:
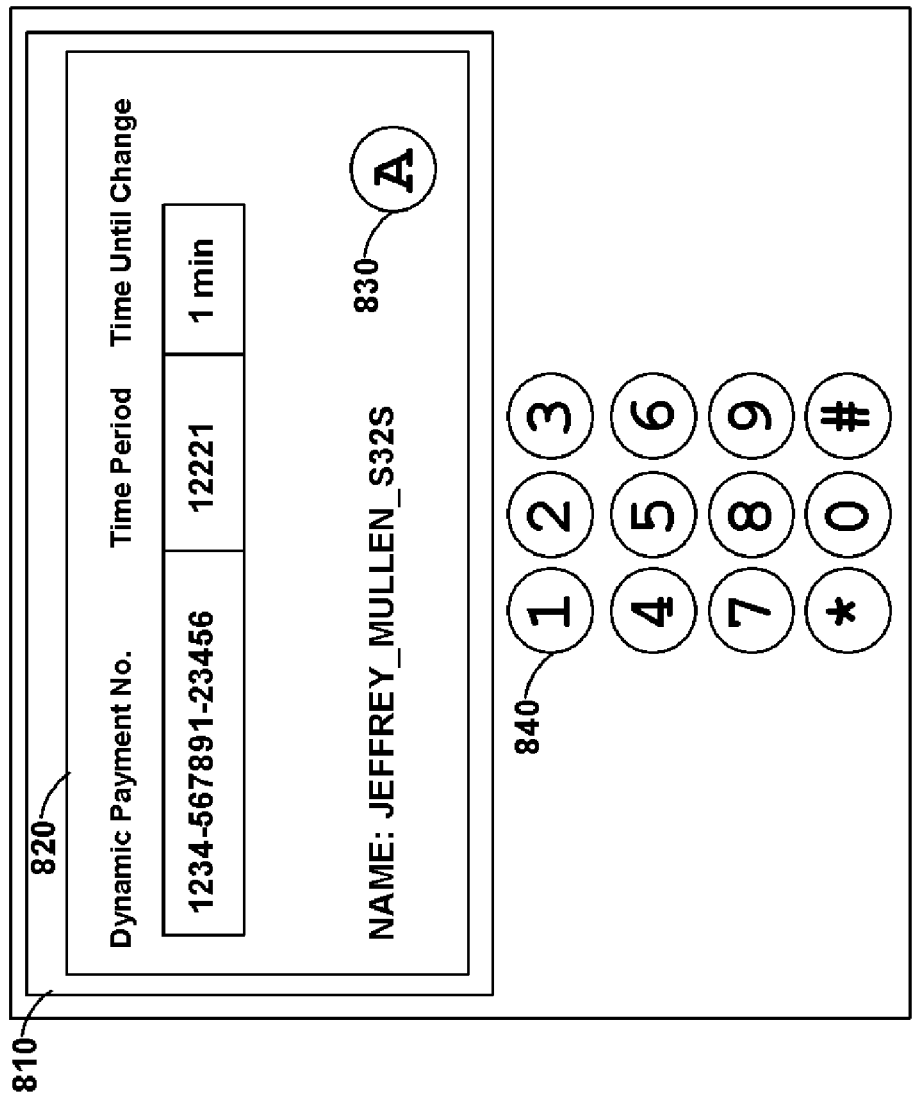
FIG. 8 is an illustration of a personal electronic device constructed in accordance with the principles of the present invention.

FIG. 8 shows personal electronic device 800 which may be, for example, a portable telephonic device, portable media player, or any type of electronic device. Persons skilled in the art will appreciate that the functionality of a card may be provided on a personal device and displayed through a graphical user interface. Personal electronic device 800 may include, for example, user inputs 840 and display 810. Virtual card 820 may be displayed on display 820. Display 820 may be a touch-sensitive display such that, for example, virtual button 830 may be provided on virtual card 820. Persons skilled in the art will appreciate that cards may be provided as virtual cards and a user may interact with such virtual cards in order to provide a variety of functions. Personal electronic device 800 may communicate to a card reader such as, for example, an RFID reader.

Persons skilled in the art will appreciate that a dynamic magnetic communications device (e.g., a magnetic emulator or magnetic encoder) may be fabricated, either completely or partially, in silicon and provided as a silicon-based chip. Other circuitry (e.g., driving circuitry) may also be fabricated on such a silicon-based chip. A processor, such as a processor for controlling a magnetic communications device, may be, for example, a programmable processor having on-board programmable non-volatile memory (e.g., FLASH memory), volatile memory (e.g., RAM), as well as a cache. Firmware as well as payment information (e.g., dynamic numbers) may be, for example, communicated from a programming device to a processor's on-board programmable non-volatile memory (e.g., a FLASH memory) such that a card may provide a variety of functionalities. Such a processor may also have one or more power-saving operating modes, in which each operating mode turns OFF a different set of circuitry to provide different levels of power consumption. One or more power-savings modes may turn OFF, for example, one or more clocking circuitry provided on a processor. An Application-Specific Integrated Circuit (ASIC) may also be included in a card or other device to provide, for example, processing, dynamic magnetic communications, as well as driving capabilities.

Persons skilled in the art will also appreciate that the present invention is not limited to only the embodiments described. Instead, the present invention more generally involves dynamic information. Persons skilled in the art will also appreciate that the apparatus of the present invention may be implemented in other ways then those described herein. All such modifications are within the scope of the present invention, which is limited only by the claims that follow.

What is claimed is:

1. A payment card comprising:
   a battery;
   a first track area operable to communicate a first track of magnetic stripe information, wherein said first track area includes:
      a first electronic device operable to provide a first portion of said first track of magnetic stripe information without using a magnetic stripe;
      a magnetic stripe operable to provide a second portion of said first track of magnetic stripe information, wherein said magnetic stripe is located to one side of said first electronic device and said magnetic stripe is not located over said first electronic device; and
   a second track area operable to communicate a second track of magnetic stripe information, wherein said second track area includes a second electronic device operable to provide said second track of magnetic stripe information without using a magnetic stripe, wherein said magnetic stripe is not located over said second electronic device.

2. The payment card of claim 1, further comprising a first display, wherein at least a portion of said first portion is displayed on said first display.

3. The payment card of claim 1, further comprising:
   a first display; and
   a second display, wherein at least a portion of said second track of magnetic stripe information is displayed on said second display.

4. The payment card of claim 1, further comprising:
   a first display, wherein at least a portion of said first portion is displayed on said first display; and
   a second display, wherein at least a portion of said second track of magnetic stripe information is displayed on said second display.

5. The payment card of claim 1 further comprising a processor.

6. The payment card of claim 1 further comprising:
   a user interface; and
   a processor.

7. The payment card of claim 1 further comprising:
   a first display; and
   a second display, wherein at least one of said first and second displays is a touch sensitive display.

8. The payment card of claim 1 further comprising:
   a first display; and
   a second display, wherein said first display displays at least a portion of a payment card number and said second display displays at least a portion of a security code number.

9. The payment card of claim 1, further comprising:
   a processor; and
   a first display, wherein said processor is operative to change data displayed on said first display, and wherein said first electronic device is operative to communicate said changed data.

10. The payment card of claim 1, further comprising:
    a processor;
    a first display; and
    a second display, wherein said processor is operative to change data displayed on said second display, and wherein said second electronic device is operative to communicate said changed data.

11. The payment card of claim 1 further comprising:
    a first user interface; and
    a first display, wherein at least a portion of said first portion is displayed on said first display based on a signal from said first user interface.

12. The payment card of claim 1 further comprising:
    a first user interface;
    a first display, wherein at least a portion of said first portion is displayed on said first display based on a signal from said first user interface;
    a second user interface; and
    a second display, wherein at least a portion of said second track of magnetic stripe information is displayed on said second display based on a signal from said second user interface.

13. The payment card of claim 1 further comprising:
    a third track area for communicating a third track of magnetic stripe information, wherein said third track area includes:
       a third electronic device for providing a first portion of said third track of magnetic stripe information; and
       a second magnetic stripe for providing a second portion of said third track of magnetic stripe information, wherein said second magnetic stripe is located to one side of said third electronic device and said second magnetic stripe is not located over said third electronic device.

14. The payment card of claim 1, further comprising an RFID antenna.

15. The payment card of claim 1, further comprising:
    an RFID antenna; and
    an IC chip.

16. The payment card of claim 1, further comprising:
    an RFID antenna;
    an IC chip; and
    a processor.

17. The payment card of claim 1, further comprising:
    an RFID antenna;
    an IC chip;
    a processor; and
    a first button.

18. The payment card of claim 1, further comprising:
    an RFID antenna;
    an IC chip;
    a processor;
    a first button; and
    a second button.

* * * * *